United States Patent
Mouchawar et al.

(10) Patent No.: US 6,862,476 B2
(45) Date of Patent: Mar. 1, 2005

(54) IMPLANTABLE CARDIAC STIMULATION DEVICE HAVING AUTOMATIC SENSITIVITY CONTROL AND METHOD

(75) Inventors: Gabriel A. Mouchawar, Valencia, CA (US); James D. Causey, III, Simi Valley, CA (US); Kelly H. McClure, Simi Valley, CA (US); J. Christopher Moulder, Sherman Oaks, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 522 days.

(21) Appl. No.: 10/081,709

(22) Filed: Feb. 20, 2002

(65) Prior Publication Data
US 2003/0158586 A1 Aug. 21, 2003

(51) Int. Cl.[7] .................................................. A61N 1/37
(52) U.S. Cl. ........................................ 607/27; 600/518
(58) Field of Search .................... 607/4, 5, 9, 17–28; 600/510, 515, 518

(56) References Cited

U.S. PATENT DOCUMENTS

| | | | |
|---|---|---|---|
| 4,880,004 A | 11/1989 | Baker, Jr. et al. | 128/419 PG |
| 4,903,699 A | 2/1990 | Baker, Jr. et al. | 128/419 PG |
| 5,226,414 A | 7/1993 | Vandegriff et al. | 128/419 PG |
| 5,269,300 A | 12/1993 | Kelly et al. | 607/4 |
| 5,339,820 A | 8/1994 | Henry et al. | 128/696 |
| 5,466,254 A | 11/1995 | Helland | 607/123 |
| 5,573,550 A | 11/1996 | Zadeh et al. | 607/28 |
| 5,685,315 A | 11/1997 | McClure et al. | 128/708 |
| 5,755,738 A | 5/1998 | Kim et al. | 607/9 |
| 5,779,645 A | 7/1998 | Olson et al. | 600/518 |
| 5,882,352 A * | 3/1999 | Duncan et al. | 607/4 |
| 5,944,744 A | 8/1999 | Paul et al. | 607/9 |
| 6,445,949 B1 * | 9/2002 | Kroll | 607/4 |

FOREIGN PATENT DOCUMENTS

| | | | |
|---|---|---|---|
| EP | 0 958 843 A1 | 11/1999 | A61N/1/37 |
| EP | 1 072 284 A2 | 1/2001 | A61N/1/37 |

OTHER PUBLICATIONS

St. Jude Medical, Tachycardia Training, pp: 12–23 (Jul. 17–20, 2000).

* cited by examiner

Primary Examiner—Jeffrey R. Jastrzab

(57) ABSTRACT

An implantable cardiac stimulation device and method provides reliable sensing of cardiac events to support cardiac pacing or fibrillation detection. The device comprises a sensing circuit that senses the cardiac events in accordance with a plurality of threshold characterizing parameters. A parameter control adjusts the threshold parameters responsive to the rate of the sensed cardiac events in a manner which precludes positive feedback to prevent continued oversensing, undersensing, or noise sensing.

53 Claims, 4 Drawing Sheets

ZONE 1 (RATE<140 BPM)

ZONE 2 (140<RATE<200 BPM)

ZONE 3 (RATE>200 BPM)

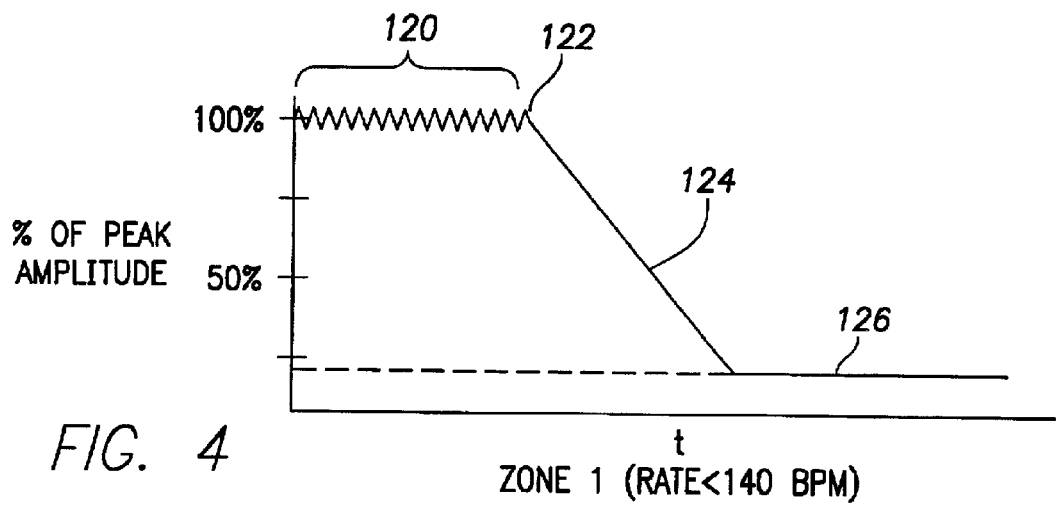
FIG. 4  ZONE 1 (RATE<140 BPM)
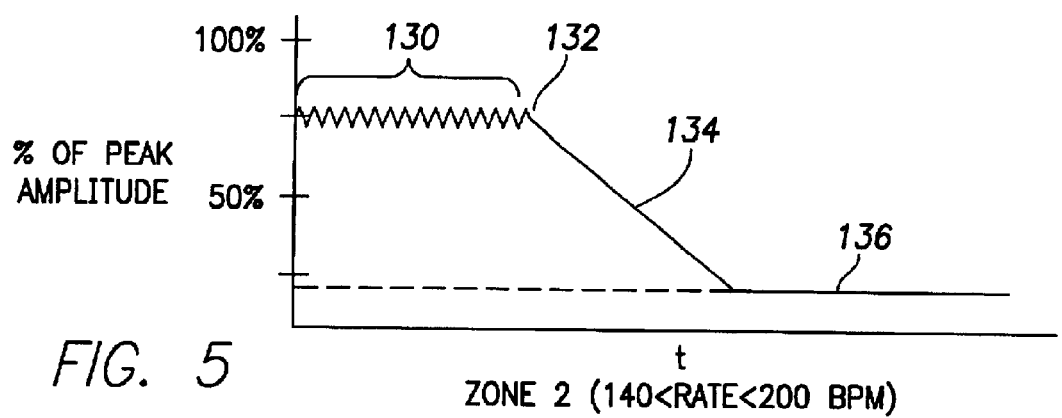
FIG. 5  ZONE 2 (140<RATE<200 BPM)
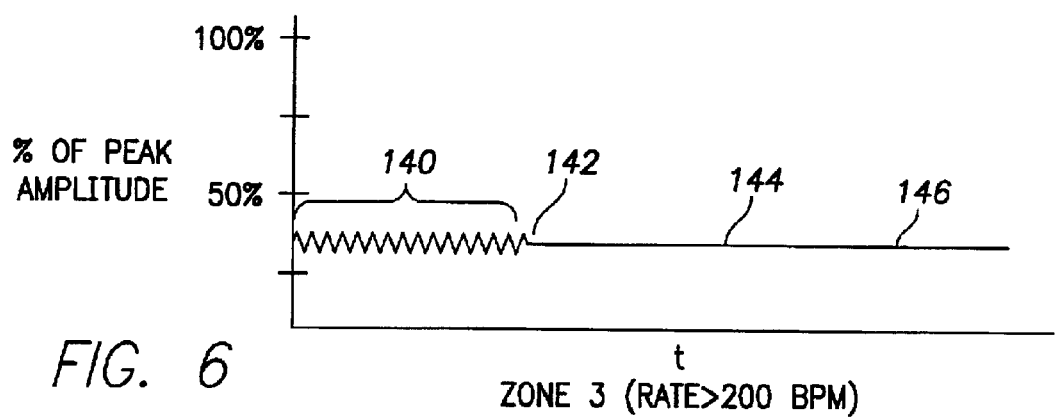
FIG. 6  ZONE 3 (RATE>200 BPM)

IMPLANTABLE CARDIAC STIMULATION DEVICE HAVING AUTOMATIC SENSITIVITY CONTROL AND METHOD

FIELD OF THE INVENTION

The present invention generally relates to an implantable cardiac stimulation device. The present invention more particularly relates to such a device and method providing automatic sensitivity control.

BACKGROUND OF THE INVENTION

Combined implantable ventricular defibrillator and pacemaker stimulation devices are well known in the art. Such devices permit a heart to be paced for treating bradycardia, for example, while also detecting for ventricular fibrillation and ventricular tachycardia and applying defibrillating electrical energy, cardioversion shocks or antitachycardia pacing pulses to the heart when fibrillation or tachycardia is detected.

One problem that must be addressed in such devices is the need to reliably sense R waves to support fibrillation detection. To this end, implantable cardiac devices including defibrillation capability generally include an automatic sensing control. The aim of such control is to maintain the sensitivity setting low enough (sensitive enough) for detecting low amplitude R wave electrical activity of the heart during fibrillation while avoiding over-sensing which could result in a T wave or noise being sensed by the pacemaker and mistaken for an R wave.

In the prior art, automatic sensing control has been performed by first establishing a ventricular refractory period (VREF) upon sensing an R wave and continuing the VREF for a pre-determined time such as 100 to 140 milliseconds. Following the VREF, the sensing threshold is set at an initial level and then decreased thereafter from the initial threshold level to a minimum threshold level where it is held until the next paced or sensed event. The initial threshold, refractory period, threshold decay rate, and minimum threshold are selected so that the threshold is above the amplitude of the T waves or noise when they occur.

These sensing parameters can be initially set toward achieving the desired sensing threshold characteristics. Unfortunately, many automatic sensing controls have parameters optimized for sensing during normal sinus rhythm and not optimized for sensing to support fibrillation detection. These systems might undersense during fibrillation resulting in a fibrillation episode going undetected. To overcome this, once initially set, the initial threshold may be varied as a function of rate and amplitude of a sensed event. More specifically, the initial threshold is decreased with decreased event amplitude and increasing rate which is generally associated with decreased event amplitudes. This would seem to be the correct course of action, to make sensing more sensitive with decreased amplitude and increased rate. However such processes are unstable because of positive feedback. Once there is false sensing, such as in sensing noise, these processes become more sensitive resulting in further sensing of noise. This continued false sensing can result in the false detection of fibrillation.

SUMMARY OF THE INVENTION

An implantable cardiac stimulation device and method are described wherein automatic sensing control is provided by varying a plurality of the automatic sensing control parameters as a function of event amplitude and rate. More specifically, in accordance with the present invention, the parameters are varied in a manner that avoids positive feedback to preclude oversensing and false fibrillation detection. The sensing parameters include initial threshold, threshold decay slope, and minimum threshold.

The parameters may be varied in sets, with each set of parameters corresponding to a different one of slow rate, medium rate, and fast rate. The parameter sets are arranged so that the initial threshold is decreased with decreased event amplitude and increased rate, the threshold decay slope is decreased with increased rate, and the minimum threshold is increased with increased rate until, at a highest rate zone, the initial threshold and minimum threshold are equal with the threshold decay slope being zero. This essentially disables automatic sensing control and maintains a constant sensing threshold.

In accordance with the present invention, positive feedback is avoided because undersensing causes the minimum threshold to be reduced and oversensing results in an increase in the minimum threshold. Hence, if oversensing occurs, it will not cause further oversensing. If undersensing occurs, it will not cause further undersensing.

BRIEF DESCRIPTION OF THE DRAWINGS

Further features and advantages of the present invention may be more readily understood by reference to the following description taken in conjunction with the accompanying drawings, in which:

FIG. 4 is a graph illustrating the automatically controlled sensing threshold as a function of time for a cardiac cycle having a slow rate in accordance with the preferred embodiment of the present invention;

FIG. 5 is another graph illustrating the automatically controlled sensing threshold as a function of time for a cardiac cycle having a medium rate in accordance with the preferred embodiment of the present invention; and FIG. 6 is a further graph illustrating the automatically controlled sensing threshold as a function of time for a cardiac cycle having a fast rate in accordance with the preferred embodiment of the present invention.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
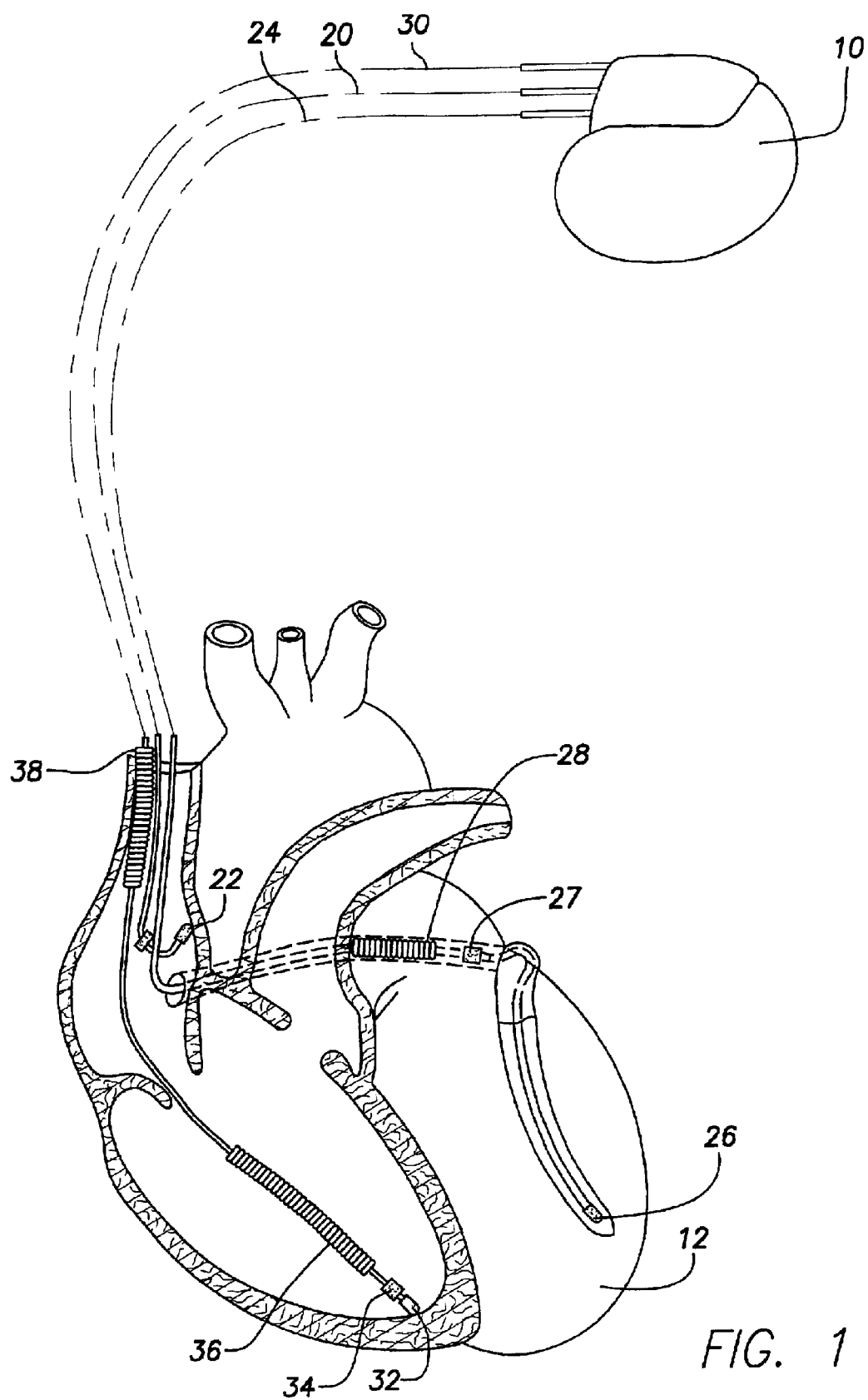
FIG. 1 is a simplified diagram illustrating an implantable stimulation device embodying the present invention in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the venus vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
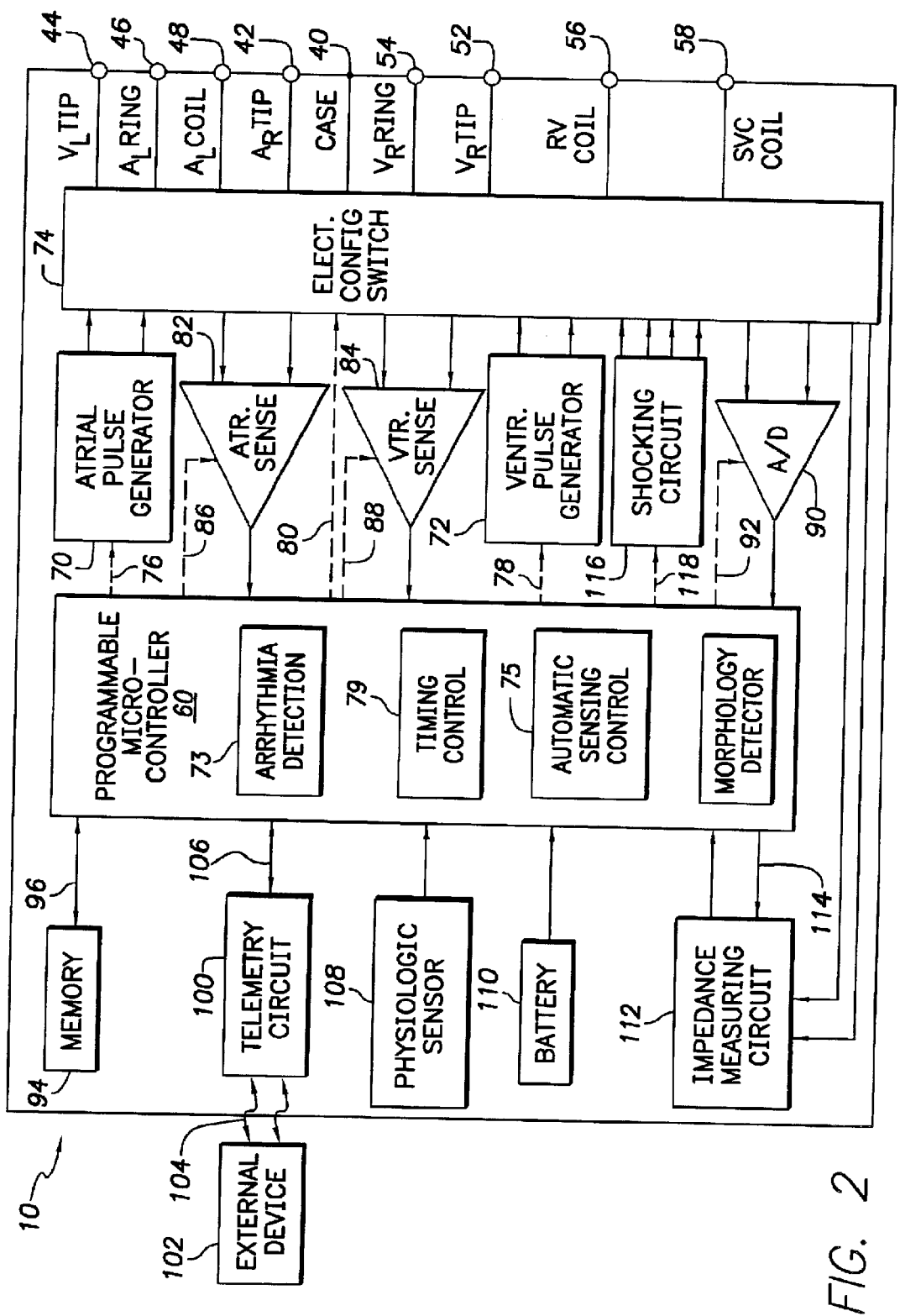
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further comprises a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector comprises at least a right atrial tip terminal ($A_R$ TIP) 42 adapted for connection to the atrial tip electrode 22.

To achieve left chamber sensing, pacing and shocking, the connector comprises at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further comprises a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically comprises a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 comprises the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further comprises timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The microcontroller 60 still further comprises an automatic sensing control 75 for controlling the sensing threshold of either one or both of the sensing circuits 82 and 84 in accordance with this preferred embodiment of the present invention. As will be seen hereinafter, the automatic sensing control (ASC) 75 sets the sensing thresholds to cause reliable event sensing to support fibrillation detection.

The switch 74 comprises a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers, bandpass filtering, and a threshold detection circuit, as known in the art. The gain or sensitivity of the circuits 82 and 84 is preferably controlled by the automatic sensing circuit 75 embodying the present invention in a manner to be more particularly described subsequently. The automatic sensing control 75 enables the circuits 82 and 84 to selectively sense the cardiac signal and events of interest. The automatic sensing control 75 hence enables the device 10 to deal effectively with the difficult problem of sensing cardiac events under low amplitude signal conditions as may be seen, for example, during atrial or ventricular fibrillation, without also sensing T waves. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art, and from the ASC 75 for controlling the sensing thresholds or sensitivity.

For arrhythmia detection, the device 10 comprises arrhythmia detection 73 which utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events determined by the arrhythmia detection 73 (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). The timing intervals between sensed events are further used by the ASC 75 to control the sensing threshold parameters it provides to the sense circuits 82 and 84.

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The memory 94 may further be used to maintain a look-up table of sensing parameters for use by the ASC 75. The look-up table may include, in accordance with this embodiment, sets of sensing parameters wherein each set corresponding to one of three different rate zones: slow rate; medium rate; and fast rate. The parameters maintained for each rate zone preferably include a percentage of event amplitude to determine initial threshold, threshold decay slope, and minimum threshold.

In the preferred embodiment, the stimulation device 10 further comprises a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally comprises a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse (preferably, in excess of 2 A, at voltages above 2 V, for periods of 10 seconds or more). The battery 110 must also have a predictable discharge characteristic so that elective replacement time can be detected. Accordingly, the device 10 may employ, for example, lithium/silver vanadium oxide batteries.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
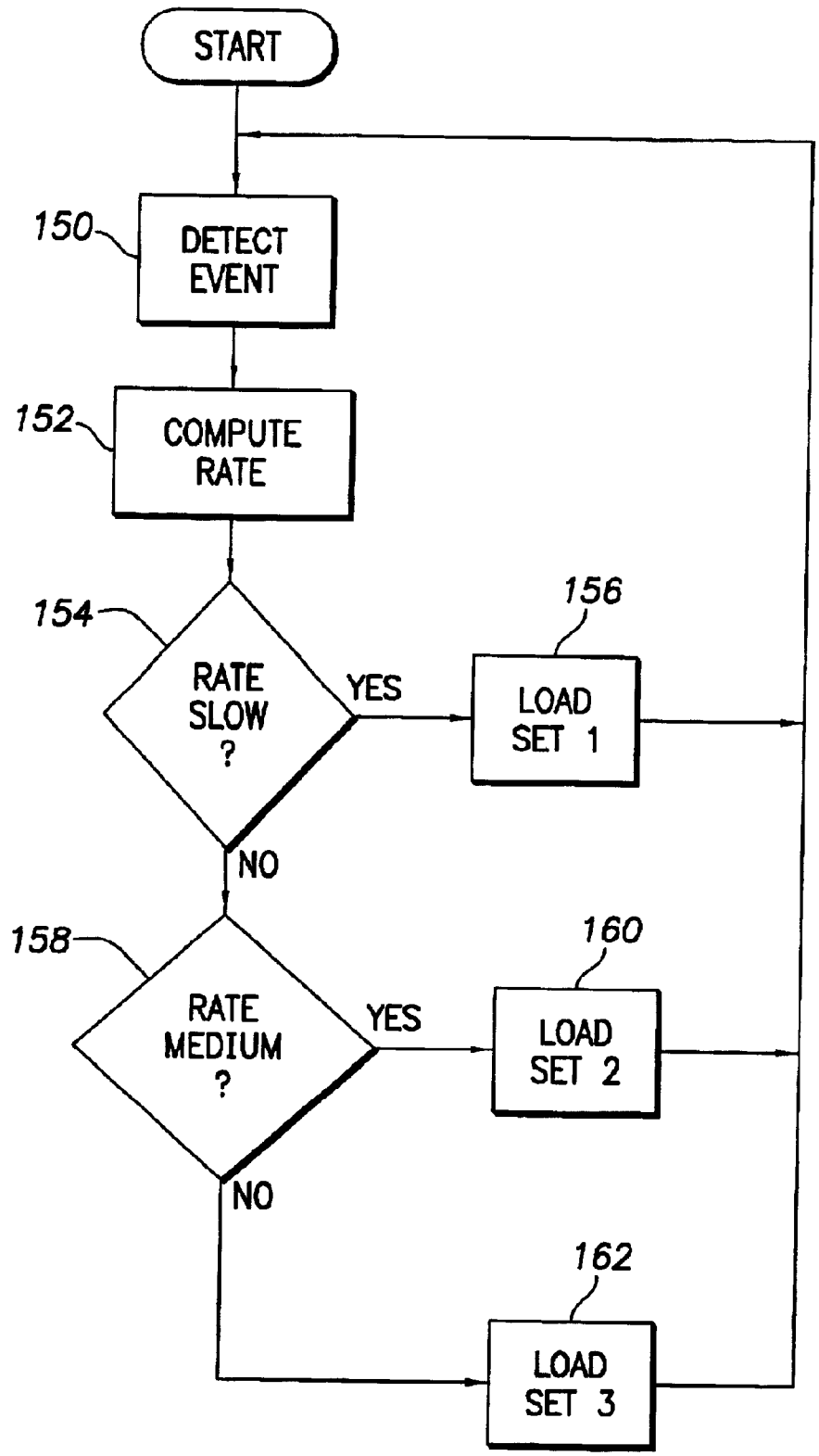
FIG. 3 is a flow chart describing an overview of the operation of one automatic sensing control embodiment of the present invention.

In FIG. 3, a flow chart is shown describing an overview of the operation and novel features implemented in one embodiment of the device 10. In this flow chart the various algorithmic steps are summarized in individual "blocks". Such blocks describe specific actions or decisions that must be made or carried out as the algorithm proceeds. Where a microcontroller (or equivalent) is employed, the flow chart presented herein provide the basis for a "control program" that may be used by such a microcontroller (or equivalent) to effectuate the desired control of the stimulation device. Those skilled in the art may readily write such a control program based on the flow charts and other descriptions presented herein.

Before the process illustrated in FIG. 3 is implemented, the sensing parameters are first loaded into a look-up table in the memory 94 for each of a plurality of rate zones. In accordance with this embodiment, and as an example, the rate zones include a slow rate zone, a medium rate zone, and a fast rate zone. The parameters in the look-up table results in threshold characteristic as illustrated in FIGS. 4–6.

FIG. 4 shows the threshold characteristic for the slow rate zone (zone 1). This zone corresponds to cardiac rate below 140 beats per minute (BPM). The parameters result in a refractory period 120 on the order of 125 milliseconds which is constant for each of the zones. The parameters further include an initial threshold 122 equal to 100% of the peak amplitude of the last event sensed, a threshold decay slope 124 equal to, for example, 200 mV/15.6 ms, and a minimum threshold 126 of, for example, 0.4 millivolts.

FIG. 5 shows the threshold characteristic for the medium rate zone (zone 2). This zone corresponds to cardiac rate between 140 and 200 beats per minute (BPM). The parameters result in a refractory period 130 on the order of 125 milliseconds. The parameters further include an initial threshold 132 equal to 75% of the peak amplitude of the last event sensed, a threshold decay slope 134 equal to, for example, 200 mV/31.2 ms, and a minimum threshold 136 of, for example, 0.6 millivolts.

Lastly, FIG. 6 shows the threshold characteristic for the fast rate zone (zone 3). This zone corresponds to cardiac rate above 200 beats per minute (BPM). The parameters result in a refractory period 140 on the order of 125 milliseconds. The parameters further include an initial threshold 142 equal to 25–50% of the peak amplitude of the last event sensed, a threshold decay slope 144 of zero, and a minimum threshold 146 equal to the initial threshold 142. Preferably, the minimum threshold is not permitted to be less than 0.8 millivolts.

As may be seen from the foregoing, while the initial threshold is decreasing with increasing rate, the minimum threshold is increasing. This precludes positive feedback and continued over, under, or noise sensing. It may be further noted that for fast rates (greater than 200 BPM) the automatic sensitivity adjustment is essentially disabled. The foregoing results in the parameters being varied in such a manner as to prevent continued over, under, and noise sensing and to promote reliable event sensing in support of fibrillation detection. If noise is sensed while a sensing circuit is under control of the relatively high sensitivity parameters in a low rate zone, the noise will be taken for an increased rate. This will cause the sensing circuit control parameters to be switched to the lower sensitivity settings of a higher rate zone. The higher rate zone sensing parameters will thus decrease the sensing circuit sensitivity so that the noise will no longer be sensed.

Turning now to FIG. 3, the automatic sensing control embodying the present invention initiates with activity block 150 wherein an event is sensed. The event sensed may be an R wave sensed by sense circuit 84 to support ventricular pacing or fibrillation detection or a P wave sensed by sense circuit 82 to support atrial pacing or fibrillation detection. Once the event is sensed, the process advances to activity block 152 wherein the cardiac rate for the last cycle is computed.

After the rate is computed in accordance with activity block 152, the process advances to decision block 154. Here it is determined if the computed rate is below 140 BPM and in the slow rate zone (zone 1). If it is, the process proceeds to activity block 156 wherein the zone 1 parameters (SET 1) are loaded from the look-up table in memory 94 into the appropriate sense circuit 82 or 84. This results in the sensing threshold characteristic previously described with reference to FIG. 4. Once the parameters are loaded, the process returns to activity block 156 for the sensing of the next event.

If the cardiac rate is not within the slow rate zone, the process continues to decision block 158. Here it is determined if the cardiac rate is within the medium rate zone (zone 2) corresponding to rates between 140 and 200 BPM.

If it is, the process advances to activity block 160 wherein the zone 2 parameters (SET 2) are loaded from the look-up table into the appropriate sense circuit 82 or 84. This results in the sensing threshold characteristic previously described with reference to FIG. 5. Once the parameters are loaded, the process returns to activity block 150 for the sensing of the next event.

If the cardiac rate is also not within the medium rate zone, the rate must be within the fast rate zone. Accordingly, the process advances to activity block 162 wherein the zone 3 parameters (SET 3) are loaded from the look-up table into the appropriate sense circuit 82 or 84. This results in the constant sensing threshold characteristic previously described with reference to FIG. 6. Once the parameters are loaded, the process returns to activity block 150 for the sensing of the next event.

As will be appreciated by those skilled in the art, instead of loading new parameters after each cycle, new parameters may be loaded only if there is a change in the rate zone. Further, although only three zones are described herein, any number of zones may be employed without departing from the present invention.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
   a sensing circuit that senses cardiac activity of a heart under control of a plurality of sensing parameters;
   a pulse generator that applies electrical energy to the heart; and
   a processor that is connected to the sensing circuit and that is operative to adjust at least one of the sensing parameters based on an amplitude value and rate of sensed cardiac events of the sensed cardiac activity.

2. The device of claim 1 wherein the sensing circuit senses ventricular events of the heart.

3. The device of claim 1 wherein the sensing circuit senses atrial events of the heart.

4. The device of claim 1 wherein the sensing circuit has an initial sensing threshold, wherein the initial sensing threshold is one of the plurality of sensing parameters, and wherein the processor adjusts the initial sensing threshold in response to sensed cardiac event amplitude.

5. The device of claim 4 wherein the processor also decreases the initial sensing threshold in response to increased sensed cardiac event rate.

6. The device of claim 4 wherein the processor adjusts the initial sensing threshold in accordance with a percentage of the sensed cardiac event amplitude.

7. The device of claim 6 wherein the processor decreases the percentage of the sensed cardiac event amplitude in response to increased sensed cardiac event rate.

8. The device of claim 6 wherein the processor incrementally adjusts the percentage in accordance with sensed cardiac event rate limits.

9. The device of claim 1 wherein the sensing circuit has a sensing threshold, wherein the sensing threshold decreases from an initial sensing threshold towards a minimum threshold between sensed cardiac events and at a decay rate, the decay rate being one of the sensing parameters, and wherein the processor adjusts the decay rate in response to sensed cardiac event rate.

10. The device of claim 9 wherein the processor decreases the decay rate responsive to increased sensed cardiac event rate.

11. The device of claim 9 wherein the processor incrementally adjusts the decay rate in accordance with sensed cardiac event rate limits.

12. The device of claim 9 wherein the minimum threshold is one of the plurality of sensing parameters and wherein the processor increases the minimum threshold responsive to increased sensed cardiac event rate.

13. The device of claim 9 wherein the minimum threshold is one of the plurality of sensing parameters and wherein the processor incrementally adjusts the minimum threshold in accordance with sensed cardiac event rate limits.

14. The device of claim 1 further comprising a fibrillation detector that detects fibrillation of the heart in response to the sensed cardiac activity, and wherein the pulse generator applies defibrillating electrical energy to the heart in response to detected fibrillation of the heart.

15. An implantable cardiac stimulation device comprising:
   sensing means for sensing cardiac activity of a heart in accordance with a plurality of sensing parameters; and
   control means for adjusting at least one of the sensing parameters based on an amplitude and rate of sensed cardiac events of the sensed cardiac activity.

16. The device of claim 15 wherein the sensing means comprises means for sensing ventricular events of the heart.

17. The device of claim 15 wherein the sensing means comprises means for sensing atrial events of the heart.

18. The device of claim 15 wherein the sensing means has an initial sensing threshold, wherein the initial sensing threshold is one of the plurality of sensing parameters, and wherein the control means comprises means for adjusting the initial sensing threshold in response to sensed cardiac event amplitude.

19. The device of claim 18 wherein the control means further comprises means for decreasing the initial sensing threshold in response to increased sensed cardiac event rate.

20. The device of claim 18 wherein the control means further comprises means for adjusting the initial sensing threshold in accordance with a percentage of the sensed cardiac event amplitude.

21. The device of claim 20 wherein the means for adjusting comprises means for decreasing the percentage of the sensed cardiac event amplitude in response to increased sensed cardiac event rate.

22. The device of claim 20 wherein the means for adjusting comprises means for incrementally adjusting the percentage in accordance with sensed cardiac event rate limits.

23. The device of claim 15 wherein the sensing means has a sensing threshold, the sensing threshold decreasing from an initial sensing threshold towards a minimum threshold between sensed cardiac events and at a decay rate, the decay rate being one of the sensing parameters, and wherein the control means comprises means for adjusting the decay rate in response to sensed cardiac event rate.

24. The device of claim 23 wherein the means for adjusting comprises means for decreasing the decay rate responsive to increased sensed cardiac event rate.

25. The device of claim 23 wherein the means for adjusting comprises means for incrementally adjusting the decay rate in accordance with sensed cardiac event rate limits.

26. The device of claim 23 wherein the minimum threshold is one of the plurality of sensing parameters and wherein the control means comprises means for increasing the minimum threshold responsive to increased sensed cardiac event rate.

27. The device of claim 23 wherein the minimum threshold is one of the plurality of sensing parameters and wherein the control means comprises means for incrementally adjusting the minimum threshold in accordance with sensed cardiac event rate limits.

28. The device of claim 15 further comprising detecting means for detecting fibrillation of the heart in response to the sensed cardiac activity of the heart, and means for defibrillating the heart in response to detection of fibrillation of the heart.

29. In an implantable cardiac stimulation device, a method of adjusting sensing parameters used in sensing cardiac events of a heart, the method comprising:

sensing cardiac events of the heart using a set of sensing parameters;

determining an amplitude value and rate of the sensed cardiac events; and adjusting the sensing parameters based upon the amplitude value and rate of the sensed cardiac events.

30. The method of claim 29 wherein sensing comprises sensing ventricular events of the heart.

31. The method of claim 29 wherein sensing comprises sensing atrial events of the heart.

32. The method of claim 29 wherein one of the plurality of sensing parameters is initial sensing threshold and wherein adjusting comprises varying the initial sensing threshold in response to sensed cardiac event amplitude.

33. The method of claim 32 wherein varying comprises decreasing the initial sensing threshold in response to increased sensed cardiac event rate.

34. The method of claim 32 wherein adjusting comprises varying the initial sensing threshold in accordance with a percentage of the sensed cardiac event amplitude.

35. The method of claim 34 wherein varying comprises decreasing the percentage of the sensed cardiac event amplitude in response to increased sensed cardiac event rate.

36. The method of claim 34 wherein adjusting comprises incrementally varying the percentage in accordance with sensed cardiac event rate limits.

37. The method of claim 29 wherein the sensing parameters comprise at least one of sensing threshold, decay rate, and minimum threshold, wherein the sensing threshold decreases from an initial sensing threshold towards the minimum threshold between sensed cardiac events at the decay rate, and wherein adjusting comprises varying the decay rate in response to sensed cardiac event rate.

38. The method of claim 37 wherein varying comprises decreasing the decay rate responsive to increased sensed cardiac event rate.

39. The method of claim 37 wherein varying comprises incrementally adjusting the decay rate in accordance with sensed cardiac event rate limits.

40. The method of claim 37 wherein adjusting comprises increasing the minimum threshold responsive to increased sensed cardiac event rate.

41. The method of claim 37 wherein adjusting comprises incrementally varying the minimum threshold in accordance with sensed cardiac event rate limits.

42. A sensing system that senses cardiac events for use in an implantable cardiac stimulation device, the system comprising:

a sensing circuit that senses cardiac events of a heart using a plurality of sensing parameters; and a processor that adjusts at least one of the sensing parameters in response to an amplitude value and rate of the sensed cardiac events.

43. The system of claim 42 wherein the sensing circuit senses either atrial or ventricular events of the heart.

44. The system of claim 42 wherein the sensing circuit has an initial sensing threshold, wherein the initial sensing threshold is one of the plurality of sensing parameters, and wherein the processor adjusts the initial sensing threshold in response to sensed cardiac event amplitude.

45. The system of claim 44 wherein the processor also decreases the initial sensing threshold in response to increased sensed cardiac event rate.

46. The device of claim 44 wherein the processor adjusts the initial sensing threshold in accordance with a percentage of the sensed cardiac event amplitude.

47. The system of claim 46 wherein the processor decreases the percentage of the sensed cardiac event amplitude in response to increased sensed cardiac event rate.

48. The system of claim 46 wherein the processor incrementally adjusts the percentage in accordance with sensed cardiac event rate limits.

49. The system of claim 42 wherein the sensing circuit has a sensing threshold, wherein the sensing threshold decreases from an initial sensing threshold toward a minimum threshold between sensed cardiac events and at a decay rate, the decay rate being one of the sensing parameters, and wherein the processor adjusts the decay rate in response to sensed cardiac event rate.

50. The system of claim 49 wherein the processor decreases the decay rate responsive to increased sensed cardiac event rate.

51. The system of claim 49 wherein the processor incrementally adjusts the decay rate in accordance with sensed cardiac event rate limits.

52. The system of claim 49 wherein the minimum threshold is one of the plurality of sensing parameters and wherein the processor increases the minimum threshold responsive to increased sensed cardiac event rate.

53. The system of claim 49 wherein the minimum threshold is one of the plurality of sensing parameters and wherein the processor incrementally adjusts the minimum threshold in accordance with sensed cardiac event rate limits.

* * * * *